(12) United States Patent
Liu et al.

(10) Patent No.: US 10,591,399 B2
(45) Date of Patent: Mar. 17, 2020

(54) METHODS FOR ANALYZING NATURAL GAS FLOW IN SUBTERRANEAN RESERVOIRS

(71) Applicant: Aramco Services Company, Houston, TX (US)

(72) Inventors: Hui-Hai Liu, Katy, TX (US); Bitao Lai, Katy, TX (US); Jinhong Chen, Katy, TX (US); Daniel T. Georgi, Houston, TX (US)

(73) Assignee: Saudi Arabian Oil Company (SA)

( * ) Notice: Subject to any disclaimer, the term of this patent is extended or adjusted under 35 U.S.C. 154(b) by 724 days.

(21) Appl. No.: 15/212,680

(22) Filed: Jul. 18, 2016

(65) Prior Publication Data

US 2017/0016812 A1 Jan. 19, 2017

Related U.S. Application Data

(60) Provisional application No. 62/194,037, filed on Jul. 17, 2015, provisional application No. 62/253,175, filed on Nov. 10, 2015.

(51) Int. Cl.
*G01N 15/08* (2006.01)
*E21B 49/02* (2006.01)

(52) U.S. Cl.
CPC ......... *G01N 15/0826* (2013.01); *E21B 49/02* (2013.01)

(58) Field of Classification Search
USPC .................................................. 324/333–356
See application file for complete search history.

(56) References Cited

U.S. PATENT DOCUMENTS

| 6,309,550 B1 | 10/2001 | Iversen et al. |
| 8,863,587 B2 | 10/2014 | Cadalen |
| 8,924,029 B2 | 12/2014 | Nath et al. |

(Continued)

FOREIGN PATENT DOCUMENTS

| CN | 2098684 U | 3/1992 |
| RU | 2003076 C1 | 11/1993 |
| WO | 2014123966 A1 | 8/2014 |

OTHER PUBLICATIONS

Zeynaly-Andabily et al. "Measurement of permeability of tight rocks", Meas. Sci. Technol. 6, 1995, pp. 1519-1527 (Year: 1995).*

(Continued)

*Primary Examiner* — Melissa J Koval
*Assistant Examiner* — Courtney G McDonnough
(74) *Attorney, Agent, or Firm* — Bracewell LLP; Constance G. Rhebergen

(57) ABSTRACT

The present invention relates to methods for analyzing and modeling natural gas flow in subterranean shale reservoirs. In preferred embodiments, methodologies and techniques for determining and modeling natural gas flow in shale formations using methodologies and techniques capable of determining natural gas properties related to dual-continuum flow, permeability and pressure within a subterranean shale reservoir. In some embodiments, the natural gas properties are determined by subjecting a subterranean shale reservoir sample to pulse-decay analysis. In certain embodiments, the methodologies and techniques described herein may be used in various reservoirs exhibiting macroporosity and/or microporosity, such as fractured reservoirs and carbonate reservoirs composed of reservoir fluids.

14 Claims, 7 Drawing Sheets

(56) References Cited

U.S. PATENT DOCUMENTS

| | | | |
|---|---|---|---|
| 9,109,440 | B2 | 8/2015 | Qiu et al. |
| 2011/0060563 | A1 | 3/2011 | Guenther et al. |
| 2013/0132020 | A1 | 5/2013 | Guillot et al. |
| 2015/0369719 | A1* | 12/2015 | Chertov .............. G01N 15/088 73/38 |

OTHER PUBLICATIONS

Liu, H. H., et al. "Pressure pulse-decay tests in a dual-continuum medium: Late-time behavior." Journal of Petroleum Science and Engineering, 147, 292-301. (2016).

Boelhouwer et al., "Liquid-induced pulsing flow in trickle-bed reactors", Chemical Engineering Science, 2002, vol. 57, Elsevier Science Ltd. pp. 3387-3399.

Capobianchi et al., "A new technique for measuring the Fickian diffusion coefficient in binary liquid solutions", Experimental Thermal and Fluid Science, 1998, pp. 33-47, vol. 18, Elsevier.

Cui, X., A. M. M. Bustin, and Robert M. Bustin. "Measurements of gas permeability and diffusivity of tight reservoir rocks: different approaches and their applications." Geofluids 9.3 (2009): 208-223.

Darabi, Hamed, et al. "Gas flow in ultra-tight shale strata." Journal of Fluid Mechanics 710.1 (2012): 641-658.

Dicker, A. I., and R. M. Smits. "A practical approach for determining permeability from laboratory pressure-pulse decay measurements." International Meeting on Petroleum Engineering. Society of Petroleum Engineers, 1988.

South, Francois, et al. "Molecular simulation to determine key shale gas parameters, and their use in a commercial simulator for production forecasting." EAGE Annual Conference & Exhibition incorporating SPE Europec. Society of Petroleum Engineers, 2013.

Hantush et al., "Theoretical development and analytical solutions for transport of volatile organic compounds in dual-porosity soils", Journal of Hydrology, 2003, pp. 18-42, vol. 279, Elsevier B.V.

Iliuta et al., "Gas-liquid interfacial mass transfer in trickle-bed reactors: state-of-the-art correlations", Chemical Engineering Science, 1999, pp. 5366-5645, vol. 54, Elsevier Science Ltd.

Ji et al., "Experimental Investigation of the Liquid Volumetric Mass Transfer Coefficient for Upward Gas-Liquid Two-Phase Flow in Rectangular Microchannels", Brazilian Journal of Chemical Engineering, 2010, pp. 573-582, vol. 27, No. 4.

Jin et al., "Hydrodynamics and mass transfer coefficient in three-phase air-lift reactors containing activated sludge", Chemical Engineering and Processing, 2006, pp. 608-617, vol. 45, Elsevier B.V.

Jones, S. C. "A Technique for Faster Pulse-Decay Permeability Measurements in Tight Rocks." SPE Formation Evaluation 12.1 (1997): 19-26.

Kaew-On et al., "New proposed two-phase multiplier and evaporation heat transfer coefficient correlations for R134a flowing at low mass flux in a multiport minichannel", Int. Comm. in Heat and Mass Transfer, 2012, pp. 853-860, vol. 39, Elsevier Ltd.

Kielbus-Rapala et al., "The effect of the physical properties of the liquid phase on the gas-liquid mass transfer coefficient in two- and three-phase agitates systems", Chemical Papers, 2011, pp. 185-192, vol. 65, No. 2, Institute of Chemistry.

Lee et al., "Interfacial area and liquid-side and overall mass transfer coefficients in a three-phase circulating fluidized bed", Chemical Engineering Science, 2013, pp. 203-211, vol. 100, Elsevier Ltd.

Liu et al. "On the relationship between stress and elastic strain for porous and fractured rock." International Journal of Rock Mechanics and Mining Sciences 46.2 (2009): 289-296.

Lonker et al., "Mineral-Fluid Interactions in the Reykjanes and Svartsengi Geothermal Systems, Iceland", American Journal of Science, 1993, pp. 605-670, vol. 293.

Pangarkar et al., "Particle-Liquid Mass Transfer Coefficient in Two-/Three-Phase Stirred Tank Reactors", Industrial &Engineering Chemistry Research, 2002, pp. 4141-4167, vol. 41, American Chemical Society.

Patel et al., "A Mesoscale Electrohydrodynamic-Driven Two-Phase Flow Heat Transport Device in Circular Geometry and In-Tube Boling Heat Transfer Coefficient Under Low Mass Flux" Journal of Heat Transfer, 2015, pp. 1-9, vol. 137, ASME.

Stemmet et al., "Influence of liquid viscosity and surface tension on the gas-liquid mass transfer coefficient for solid foam packings in co-current two phase flow", Chemical Eng. Research and Design, 2008, pp. 1094-1106, vol. 86, Elsevier B.V.

Trivizadakis et al., "A study of local liquid/solid mass transfer in packed beds under trickling and induced pulsing flow", Chemical Engineering Science, 2006, pp. 7684-7696, vol. 61, Elsevier Ltd.

Yang et al., "Experimental study on gas-liquid interfacial area and mass transfer coefficient in three-phase circulating fluidized beds", Chemical Engineering Journal, 2001, pp. 485-490, vol. 84, Elsevier Science B.V.

Akkutlu, I. Yucel, and Ebrahim Fathi. "Multiscale gas transport in shales with local kerogen heterogeneities." SPE Journal 17.04 (2012): 1-002.

Alnoaimi, Khalid R. "Characterization and Measurement of Multiscale Gas Transport in Shale Core Samples." Unconventional Resources Technology Conference (URTEC), 2014.

Bhandari et al., "Anisotropy and Stress Dependence of Permeability in the Barnett Shale", Transport in Porous Media, 2015, p. 393-411, vol. 108, No. 2, Springer.

Chen, "Multiscale imaging, modeling, and principal component analysis of gas transport in shale reservoirs", Fuel, 2016, p. 761-770, vol. 182, Elsevier.

International Search Report and Written Opinion for related PCT application PCT/US2016/042135 dated Sep. 29, 2016.

Cronin et al., "Dual-permeability micro-stratigraphy in the Barnett Shale" Journal of Petroleum Science and Engineering, 2016, p. 119-127, vol. 142, Elsevier.

* cited by examiner

METHODS FOR ANALYZING NATURAL GAS FLOW IN SUBTERRANEAN RESERVOIRS

CROSS-REFERENCE TO RELATED APPLICATIONS

This application claims priority from U.S. Provisional Patent Application No. 62/194,037 filed on Jul. 17, 2015 and U.S. Provisional Patent Application No. 62/253,175 filed on Nov. 10, 2015. For purposes of Untied States patent practice, this application incorporates the contents of both Provisional Patent Applications by reference in their entirety.

FIELD OF THE INVENTION

The present invention relates to methods for analyzing and modeling natural gas flow in subterranean reservoirs. In some embodiments, methodologies and techniques for determining and modeling natural gas flow in shale formations capable of determining natural gas properties related to permeability and dual-continuum flow within a subterranean reservoir are provided. In further embodiments, the natural gas properties are determined by subjecting a subterranean reservoir sample to pulse-decay analysis. In certain embodiments, the methodologies and techniques described herein can be used in various reservoirs exhibiting both macroporosity and microporosity such as shale gas reservoirs, fractured reservoirs and carbonate reservoirs composed of reservoir fluids.

BACKGROUND OF THE INVENTION

The increasing energy demands of the global economy require the identification of new hydrocarbon reservoirs as well as the maximization of hydrocarbon recovery from existing reservoirs. The identification and recovery of the vast deposits of hydrocarbons trapped within subterranean reservoir formations have long been recognized as a challenge to the industry. The accurate identification and characterization of shale gas flow is critical for assessing and maximizing shale gas recovery in challenging environments such as tight shale formations comprising shale gas enriched with organic based material.

The use of pulse-decay permeability measurements for the characterization and modeling of subterranean shale gas flow has previously been described, e.g. in Jones, "A Technique for Fast Pulse-Decay Permeability Measurements in Tight Rocks," SPEFE (March 1997) 19-25; Darabi et al., "Gas Flow in Ultra-Tight Shale Strata," Journal of Fluid Mechanics 710, 641-658 (2012) and Dicker et al., "A Practical Approach for Determining Permeability from Laboratory Pressure-Pulse Decay Measurements," 1988 SPE International Meeting on Petroleum Engineering (Paper SPE 17578).

However, these methodologies and techniques have well defined limitations in shale gas identification and analysis, particularly with regard to the characterization and modeling of shale gas flow within the numerous types of pore systems that can exist in a reservoir, including "fast-flow" and "slow-flow" pathways. The need therefore exists for improved methods and techniques for assessing subterranean shale gas reservoirs and deposits for enhancing natural gas recovery.

SUMMARY OF THE INVENTION

The present invention relates to methods for analyzing and modeling natural gas flow in subterranean reservoirs. In a first aspect of the invention, a method of determining a flow characteristic of a subterranean reservoir formation for the purpose of predicting production capabilities is provided. The method including the steps of obtaining a reservoir sample from the subterranean reservoir formation, creating a plurality of pressure pulses across the reservoir sample, obtaining from the reservoir sample dual-continuum test data, where the dual-continuum test data includes late-time stage pressure data, determining a mass transfer coefficient from the dual-continuum test data, and determining the flow characteristic from the mass transfer coefficient.

In certain aspects of the present invention, the subterranean formation is selected from the group consisting of limestone, sandstone, and shale. In certain aspects of the present invention, the dual-continuum test data is obtained from a dual-continuum test system. In certain aspects of the present invention, the step of obtaining from the reservoir sample the dual-continuum test data further includes the steps of placing the reservoir sample in a sample, where the sample is fluidly connected to an upstream gas reservoir and a downstream gas reservoir, filling the upstream gas reservoir, the downstream gas reservoir, and the sample with a gas to a gas pressure, closing an upstream valve, where closing the upstream valve isolates upstream gas reservoir from both the downstream gas reservoir and the sample, closing a downstream valve, where closing the downstream valve isolates downstream gas reservoir from both the upstream gas reservoir and the sample, increasing the pressure in the upstream gas reservoir to a test pressure, increasing the pressure in the downstream gas reservoir to the test pressure, opening the upstream valve generally at the same time the downstream valve is opened such that a plurality pressure pulse is created from the upstream gas reservoir and the downstream gas reservoir, and measuring the pressure data in the upstream gas reservoir and the downstream gas reservoir. In certain aspects of the present invention, the flow characteristic is dual-continuum flow. In certain aspects of the present invention, the flow characteristic is a function of an immobile continuum and a mobile continuum in the reservoir sample.

In a second aspect of the present invention, a method of obtaining dual-continuum test data is provided. The method includes the steps of placing a reservoir sample in a sample, where the sample is fluidly connected to an upstream gas reservoir and a downstream gas reservoir, filling the upstream gas reservoir, the downstream gas reservoir, and the sample with a gas to a gas pressure such that the gas pressure in the upstream gas reservoir, the downstream gas reservoir and the sample is uniform, closing an upstream valve, where closing the upstream valve isolates the upstream gas reservoir from both the downstream gas reservoir and the sample, closing a downstream valve, where closing the downstream valve isolates the downstream gas reservoir from both the upstream gas reservoir and the sample, increasing the pressure in the upstream gas reservoir to a test pressure, increasing the pressure in the downstream gas reservoir to the test pressure, opening the upstream valve generally at the same time the downstream valve is opened such that a plurality pressure pulse is created from the upstream gas reservoir and the downstream gas reservoir, and measuring the dual-continuum test data.

In certain aspects of the present invention, the method further includes the step of isolating the reservoir sample from a subterranean reservoir formation. In certain aspects of the present invention, the uniform gas pressure can be between 1000 psi and 10,000 psi. In certain aspects of the present invention, the gas is selected from the group consisting of carbon dioxide, helium, nitrogen, and argon.

In a third aspect of the present invention, a system to measure dual-continuum test data is provided. The system includes a sample, the sample configured to secure a reservoir sample, an upstream gas reservoir fluidly connected to the sample and a downstream gas reservoir, a downstream gas reservoir fluidly connected to the sample and the upstream gas reservoir, an upstream valve, the upstream valve configured to isolate the upstream gas reservoir from both the sample and the downstream gas reservoir, and a downstream valve, the downstream valve configured to isolate the downstream gas reservoir from both the sample and the upstream gas reservoir.

In a fourth aspect of the present invention, a method of determining a flow characteristic of a subterranean reservoir formation for the purpose of predicting production capabilities is provided. The method includes the steps of obtaining dual-continuum test data, where the dual-continuum test data represents the subterranean reservoir formation, determining a mass transfer coefficient from the dual-continuum test data, and determining the flow characteristic from the mass transfer coefficient.

BRIEF DESCRIPTION OF THE DRAWINGS

So that the manner in which the features, advantages and objects of the invention, as well as others which will become apparent, are attained, and can be understood in more detail, more particular description of the invention briefly summarized above can be had by reference to the embodiments thereof which are illustrated in the appended drawings that form a part of this specification. It is to be noted, however, that the drawings illustrate only certain embodiments of the invention and are therefore not to be considered limiting of its scope as the invention may admit to other equally effective embodiments. The present technology will be better understood on reading the following detailed description of non-limiting embodiments thereof, and on examining the accompanying drawings.

DETAILED DESCRIPTION OF THE INVENTION

Although the following detailed description contains specific details for illustrative purposes, the skilled artisan will appreciate that many examples, variations and alterations to the following details are within the scope and spirit of the invention. Accordingly, the exemplary embodiments of the invention described herein are set forth without any loss of generality, and without undue limitations, on the claimed invention.

The present invention provides methods and techniques for determining values of parameters describing gas flow in a dual-continuum shale matrix. The present invention provides a method to determine the mass transfer coefficient for gas flow in a dual-continuum matrix of a tight organic-rich shale. The present invention provides a method to identify dual-continuum characteristics from pulse-decay test data and to estimate a mass transfer coefficient between the two continua if the dual-continuum characteristic exists. The methods of the present invention use pulse-decay data.

As used herein, the term "mass transfer coefficient" refers to the mass flow rate between the two continua divided by the gas pressure difference between the two continua per unit bulk volume of shale matrix. The mass transfer coefficient is a key parameter for describing mass transfer between the two continua.

As used herein, the term "shale gas" refers to natural gas or a natural gas deposit located adjacent to or within a subterranean shale formation. Within the context of the present invention, shale gas can be identified and recovered from active hydrocarbon drilling and recovery processes such as horizontal drilling, hydraulic fracturing chemical fracturing such as slick water fracturing, or a combination of recovery processes. Shale gas can include methane, ethane, propane, butane, carbon monoxide, carbon dioxide, and combinations thereof.

Figure 2:
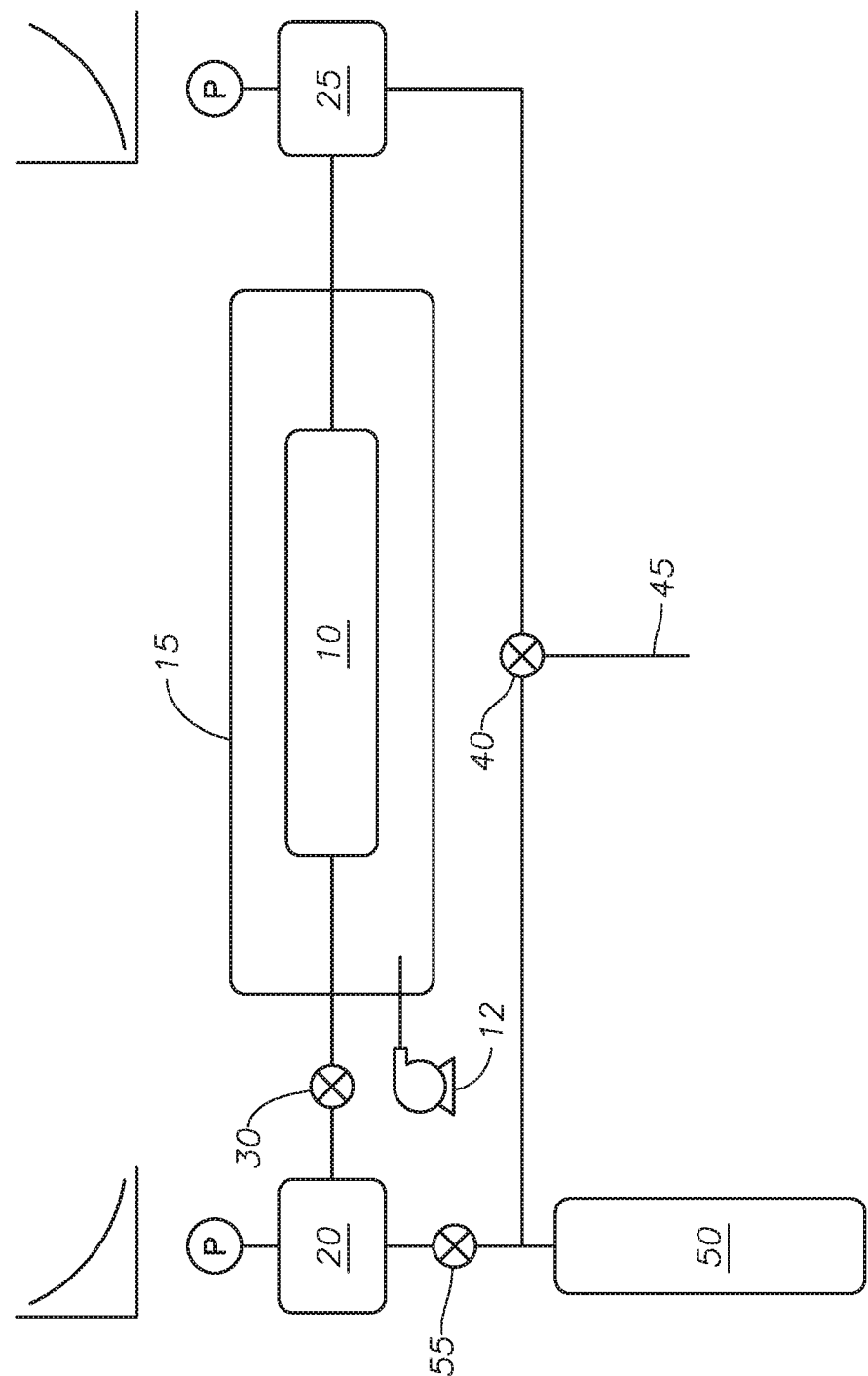
FIG. 2 shows a pulse-decay system for gathering pulse-decay test data.

The term "pulse-decay test," alternatively known as the "transient pulse method," refers to a technique for measuring the permeability of a material. A pulse-decay test uses a pulse-decay system as shown in FIG. 2. Rock sample 10 is placed in holder 15. Holder 15 can apply hydrostatic confining stress to rock sample 10. Rock sample 10 is a cylindrical sample from a reservoir formation. Rock sample 10 is fluidly connected to both upstream reservoir 20 and downstream reservoir 25. At the start of the pulse-decay test, the pulse-decay system is in equilibrium with a uniform gas pressure. Uniform gas pressure can be achieved by filling upstream reservoir 20, downstream reservoir 25, and holder 15 with a gas to a gas pressure. In at least one embodiment, the gas flows from gas reservoir 50 to fill upstream reservoir 20 and downstream reservoir 5. Examples of gases that can be used to fill the pulse-decay system include nitrogen, carbon dioxide, helium, and argon. The gas pressure can be between about 1 psi and about 10,000 psi, alternately between about 1000 psi and about 5000 psi, alternately between 1000 psi and 2000 psi. The pulse-decay system is allowed to stabilize at which point the gas pressure is a uniform gas pressure. After a uniform gas pressure is reached, valve 30 is closed, closing off the connection between upstream reservoir 20 and rock sample 10. The pressure in upstream reservoir 20 is then increased by a pressure-increase. The pressure-increase is caused by adding more gas from gas reservoir 50. In at least one embodiment, the pressure-increase is 10 psi. In at least one embodiment, the pressure-increase is at least 10 psi. When the pressure in upstream reservoir 20 becomes constant at the pressure-increase above the uniform gas pressure, gas reservoir valve 55 is closed and valve 30 is opened which initiates the pressure-transient portion of the measurement. Opening valve 30 introduces a pressure pulse from upstream reservoir 20 due to the pressure in upstream reservoir 20 being higher than the pressure in the rest of the pulse-decay system. The pressure in upstream reservoir 20 and the pressure in downstream reservoir 25 are measured and recorded as a function of time (the "pulse-decay test data"). The pressure in upstream reservoir 20 declines with time as the pressure pulse travels through rock sample 10. The step-function pressure pulse gradually becomes a smooth pressure gradient. Pressure in downstream reservoir 25 remains constant until the smoothed pressure pulse reaches the downstream end of rock sample 10, at which time pressure in downstream reservoir 25 increases. A pulse-decay test ends when the pressure in upstream reservoir 20 is nearly equal to the pressure in downstream reservoir 25 and the pressure in both stabilizes. As used here, "nearly equal to" means that the pressure in upstream reservoir 20 and the pressure in downstream reservoir 25 differ by a value less than the measurement error range. Confining pump 12 can provide a confining pressure on rock sample 10 in holder 15. Three-way valve 40 can be used to control gas flow between upstream reservoir 20 and downstream reservoir 25 and vent line 45. Three-way valve is a three-way valve that allows flow to be adjusted in multiple lines. Vent line 45 can be used to release the gas from the pulse-decay system. In accordance with the present invention, pulse-decay can be used to measure the permeability of shale rock. In preferred embodiments, pulse-decay is used to determine shale rock properties related to gas flow in a shale rock matrix, including dual-continuum gas flow.

As used herein, "stabilize" or "steady state" or "equilibrate" refers to a state where the pressure in the pulse-decay system does not change with time. The pressure in each unit of the pulse-decay system remains constant and the entire pulse-decay system equilibrates. The pressure can take between about 30 minutes and about 10 hours to stabilize.

Figure 1:
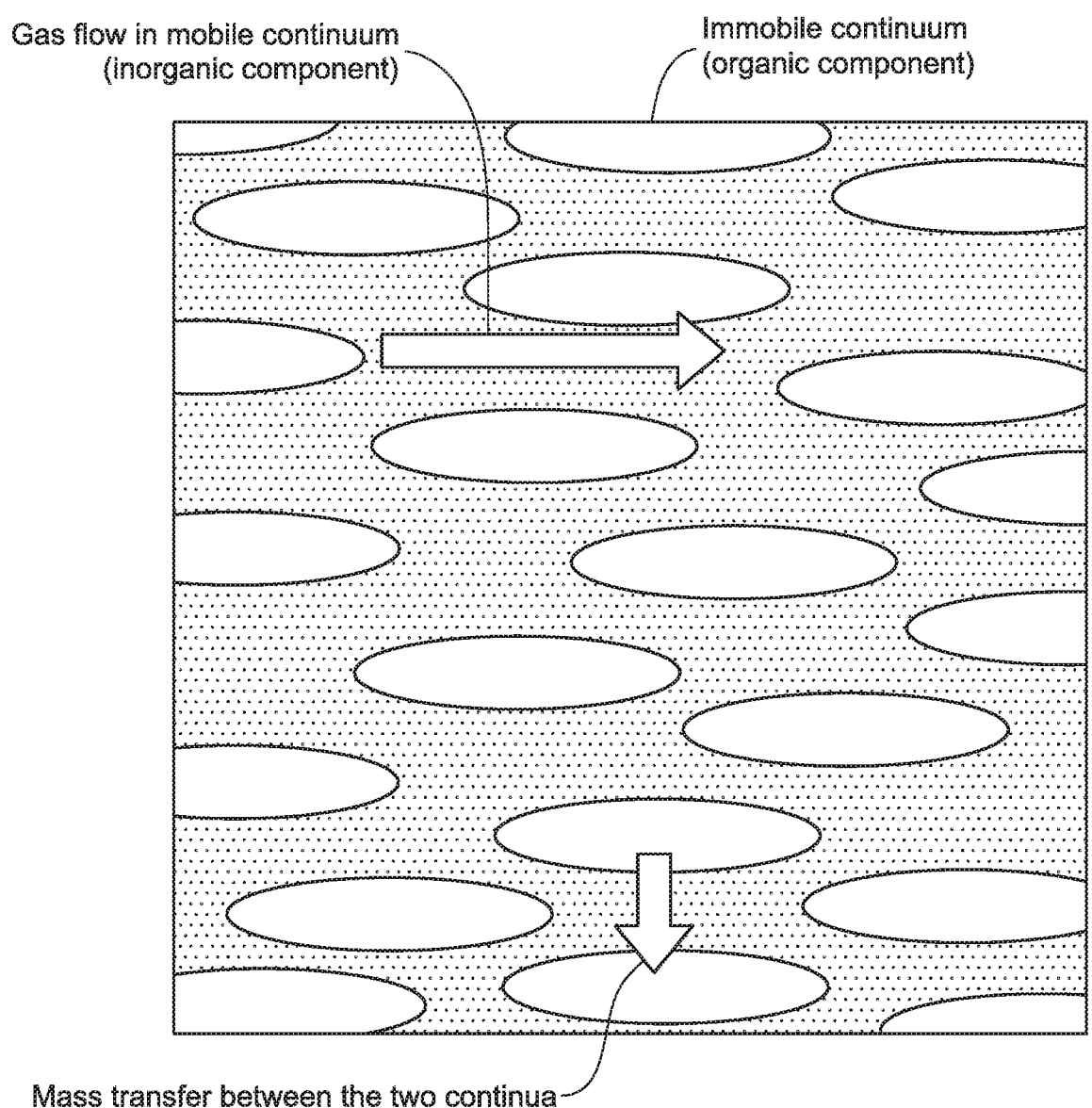
FIG. 1 shows a schematic of material transfer, for example a gas mass transfer, within a subterranean shale formation in accordance with embodiments of the present invention.

As used herein, the term "dual-continuum" refers to a dual-porosity system having one globally permeable continuum and a second that is either not globally connected or has negligible global permeability. A continuum in a subsurface material refers to a subdomain or feature, for example a feature can be a fracture network, that has similar flow and transport properties; these properties, however, are dramatically different from those in other subdomains or features within the same material. FIG. 1 illustrates flow behavior in a dual-continuum shale matrix. Dual-continuum is characterized by the properties of an organic material continuous phase (first continuum component) and the properties of an inorganic material continuous phase (second continuum component) of a subterranean reservoir. Within the context of the present invention, the mobile continuum corresponds to the inorganic component of the shale matrix while the immobile continuum corresponds to the organic component of the shale matrix as discussed in, e.g. Darabi et al., "Gas Flow in Ultra-Tight Shale Strata," *Journal of Fluid Mechanics* 710, 641-658 (2012); and Gouth et al., "Molecular simulation to determine key shale gas parameters, and their use in a commercial simulator for production forecasting," SPE Paper 164790; EAGE Annual Conference & Exhibition (London) (June 2013). In some embodiments, dual-continuum properties are associated with one or more subterranean shale matrices and their fluid properties, such as fast-flow pathways and slow-flow pathways within the shale matrix, their pore size properties including pore size distribution, and physicochemical differences between the organic material component and inorganic material component of the shale formation.

The terms "organic material", "organic component" and "organic" refer to carbonaceous materials or substrates, derived from a hydrocarbon based source or sources, having a low permeability. As used herein, the term "low permeability" is a relative term that refers to the difference in permeability between the organic component and inorganic component, with the organic component having the lower permeability. While in no way limiting the scope of the present invention, an organic material or organic component can include one or more of pre-bitumen bituminous groundmass such as the remains of woody and non-woody plants and their organic components; animals, non-animal organisms and cellular debris. An organic material or organic component, in accordance with the present invention, can be volatile or non-volatile. The organic material does not include the hydrocarbon targeted for removal from the formation.

As used herein, the terms "inorganic material", "inorganic component" and "inorganic" refer to non-hydrocarbon containing materials or substrates having a high permeability. As used herein, the term "high permeability" is a relative term that refers to the difference in permeability between the organic component and inorganic component, with the organic component having the higher permeability. In accordance with the present invention, an inorganic material or component includes but is not limited to one or more transition metals including cadmium, cobalt, chromium, mercury, nickel, iron, copper, vanadium uranium and barium; non-transition metals such as sulfur, nitrogen and arsenic; minerals such as quartz, calcite and dolomite; and the non-carbonaceous components of coke and/or semicoke.

As used herein, the term "mobile continuum" refers to the globally permeable continuum of the dual-continuum system. The mobile continuum corresponds to the inorganic component of a shale matrix.

As used herein, the term "immobile continuum" refers to the continuum that is not globally connected or has negligible global permeability in the dual-continuum system. The immobile continuum refers to the organic component of a shale matrix. The immobile continuum can be mobile for gas transport to the mobile continuum.

As used herein, the term "fast-flow pathways" refers to global permeable flow paths corresponding to high permeability in a rock sample.

As used herein, the term "slow-flow pathways" refers to the flow paths corresponding to low permeability in a rock sample.

As used herein, the term "confining pressure" or "confining stress" refers to the pressure or physical stress imposed on a rock sample.

As used herein, the terms "late-time stage" or "late-term stage" refers to the point in the dual-continuum test when any difference in the pressure among the upstream gas reservoir and downstream gas reservoir and the mobile continuum is relatively small. As used herein, "relatively small" refers to the condition that a pressure variation has a negligible impact on gas properties, such as density. One technique for analyzing pulse-decay data uses only late-term stage measurements, which requires only the first root of an otherwise infinite series to calculate permeability. The late-time stage can occur between one (1) millisecond (ms) to about one (1) week after the pressure-transient portion of the dual-continuum test is initiated.

As used herein, "uniform gas pressure" refers to the pressure in the pulse-decay system being the same throughout the pulse-decay system. When the pulse-decay system is at a uniform gas pressure, the pressure in the upstream reservoir, the downstream reservoir, and the sample are the same value. Achieving uniform gas pressure can take between about 1 minute and about 5 hours, alternately less than 1 hour, alternately less than 5 hours, alternately between about 1 hour and about 5 hours, and alternately between about 2 hours and about 4 hours.

The present invention addresses problems associated with the identification, analysis and recovery of shale gas from a shale matrix. The shale matrix can exhibit dual-continuum gas-flow behavior owing to property differences between the organic components and inorganic components in the shale matrix. In some embodiments, a reservoir sample evaluated using the present invention can be treated as a dual-continuum system for determining properties of the reservoir sample, such as mass transfer properties of shale, including fast-flow pathways and slow-flow pathways within one or more samples of interest. The present invention advantageously provides a method to estimate the mass transfer coefficient between the dual-continuum with pulse-decay. The method of the present invention allows determination of mass transfer coefficient in porous media with pulse-decay.

The present invention advantageously provides for methodologies and techniques for determining an effective mass transfer coefficient of a reservoir sample based on dual-continuum characteristics from pulse-decay test data.

A first method for estimating the mass transfer coefficient is now described with reference to FIG. 2. In some embodiments, the methodologies and techniques described herein assume that a subterranean shale reservoir sample can be characterized as a dual-continuum system that exhibits gas flow pathways, including both fast-flow pathways and slow-flow pathways and further exhibits negligible global permeability of slow-flow pathways and can therefore be characterized with respect to mass transfer processes as depicted in FIG. 1. As will be shown, because the pressure difference between upstream reservoir 20 and downstream reservoir 25 is an exponential function of time with permeability as a parameter, permeability can be based on the slope from the plot of log of the pressure difference versus time, allowing the estimation of permeability from the data generated by the pulse-decay system.

As shown therein, a dual-continuum system includes both a mobile continuum and an immobile continuum. A mass balance equation for describing the relevant properties associated with the mobile continuum of rock sample 10 is described in Equation (1):

$$\frac{\partial \rho_m}{\partial t} = \frac{\partial}{\partial x}\left(\frac{k\rho}{\mu}\frac{\partial p}{\partial x}\right) + q_{im} \quad (1)$$

wherein t is time; x is the spatial coordinate along the longitudinal direction of rock sample 10 and has a value of zero (0) at the end of rock sample 10 associated with upstream reservoir 20 and L at the end of rock sample 10 associated with downstream reservoir 25; k represents the permeability parameters for the mobile continuum; µ represents the gas viscosity; ρ represents the gas density; p represents pressure components; $q_{im}$ represents the rate of mass transfer per unit volume of the porous medium from the immobile continuum; and $\rho_m$ is the total gas density of the mobile continuum and can be expressed as shown in Equation (2):

$$\rho_m = \phi\rho + (1-\phi)\rho_a \quad (2)$$

where φ represents the porosity of the mobile continuum; and $\rho_a$ represents the absorbed gas mass per unit volume (density) of shale excluding the pore space within the mobile continuum (please see the Nomenclature section for a complete listing and associated definitions of mathematical factors, constants and operators described herein). For an inert gas, $\rho_a$=0. The parameters in Equations (1) and (2) are defined for the mobile continuum except $q_{im}$.

With regards to Equation (1), the storage term $$\left(\frac{\partial \rho_m}{\partial t}\right)$$

can alternatively be expressed as shown in Equation (3):

$$\frac{\partial \rho_m}{\partial t} = \frac{d\rho_m}{dp}\frac{\partial p}{\partial t} = A\frac{\partial p}{\partial t} \quad (3)$$

Within the context of the present invention, under isothermal conditions, $\rho_m$ is regarded solely as a function of pressure. In some embodiments, porosity can be regarded as stress dependent as described in, e.g. Liu et al., "On the Relationship Between Stress and Elastic Strain for Porous and Fractured Rock," *Int. J. Rock Mech. Min. Sci.* 46(2), 289-296 (2009). Because the pressure pulse in the pulse-decay test is small relative to the uniform pressure, rock sample 10 can be regarded as a rigid medium as described in, e.g. Darabi et al., "Gas Flow in Ultra-Tight Shale Strata," *Journal of Fluid Mechanics* 710, 641-658 (2012). Because rock sample 10 can be regarded as rigid, the porosity change can be ignored and the parameter A can be described in consideration of the contributions of gas density change in pressure as shown in shown in Equation (4):

$$A = \phi\frac{d\rho}{dp} + (1-\phi)\frac{d\rho_a}{dp} \quad (4)$$

In the late time-stage, the gas pressure in the pulse-decay system can be regarded as relatively uniform over time, such as a systematic pressure difference of between about 0.1% and about 10%, in other words, the pressure pulse is small relative to the uniform pressure and parameter A can be treated as a constant. The determination of gas mass flux with respect to the volumetric flux in rock sample 10 can be represented as shown in Equation (5):

$$q = -\frac{k\rho}{\mu}\frac{\partial p}{\partial x} = -K\frac{\partial p}{\partial x} \quad (5)$$

where K represents gas flow conductivity. In the context of the present invention, at the late-time stage gas density (ρ), gas viscosity (µ) and gas flow conductivity (K) can be regarded as constant values for the dual-continuum methodologies and techniques described herein and in, e.g. Jones, "A Technique for Fast Pulse-Decay Permeability Measurements in Tight Rocks," *SPEFE*, 19-25 (March 1997); and Cui et al., "Measurements of Gas Permeability and Diffusivity of Tight Reservoir Rocks: Different Approaches and Their Applications," *Geofluids* 9, 208-223 (2009). The gas permeability value can therefore be determined if the gas flow conductivity (K) value is known. In alternative embodiments, the incorporation of a pseudo pressure factor (p*) as a dependent variable can be used in the dual-continuum determination techniques described herein and can be expressed as shown in Equation (6):

$$p^* = \int_{P_{ref}}^{p} \frac{\rho}{\mu} dp \qquad (6)$$

where $p_{ref}$ represents a reference pressure.

In some embodiments, the pressure upon rock sample 10 can be regarded as a dependent variable to address pulse-decay in the dual continuum based methodologies and techniques described herein such that mass balance with respect to gas flow in the mobile continuum can be expressed according to Equation (7):

$$A\frac{\partial p}{\partial t} = \frac{\partial}{\partial x}\left(K\frac{\partial p}{\partial x}\right) + q_{im} \qquad (7)$$

The dual-continuum properties associated with rock sample 10 can be characterized, in accordance with embodiments of the present invention, by the mass transfer coefficient between the two continua. In the immobile continuum, the change in total gas mass per unit bulk volume for the rock sample 10 can be equated with the mass transfer rate from the immobile to the mobile continuum and can be expressed as described in Equation (8):

$$\frac{\partial \rho_{m,i}}{\partial t} = \frac{d\rho_{m,i}}{dp_i}\frac{dp_i}{dt} = B^*(p - p_i) \qquad (8)$$

where i represents the immobile continuum; $p_i$ represents gas pressure; B* is the mass transfer coefficient that is proportional to the permeability of the immobile continuum and interfacial area between the two continua, and $\rho_{m,i}$ is the total gas mass per unit volume of the porous medium associated with the immobile continuum.

At the late-time stage of the pulse-decay test, in accordance with the present invention the gas pressure associated with the mobile continuum becomes relatively uniform over time. In addition, the relative pore volume for the immobile continuum is significantly less than the total gas volume for the pulse-decay system including upstream reservoir 20 and downstream reservoir 25 such that the pressure in the mobile continuum for rock sample 10 as described in Equation (8) can be regarded as time independent and mass transfer within the sample can be expressed according to Equation (9):

$$p_i - p = Ce^{-Bt} \qquad (9)$$

where C is a constant and B can be expressed using Equation (10):

$$B = B^* \bigg/ \left(\frac{d\rho_{m,i}}{dp_i}\right) \qquad (10)$$

In accordance with some embodiments of the present invention, $$\frac{d\rho_{m,i}}{dp_i}$$

can be regarded as a constant due to the relatively low pressure variance, such as between about 1% and about 10%, in the pulse-decay system over time between upstream reservoir 20 and downstream reservoir 25. In Equation (8), B represents the apparent mass transfer coefficient that includes the effects of free and absorbed/adsorbed gas storage in the immobile continuum, with smaller B values corresponding to stronger dual-porosity behavior.

Within the context of the present invention, the immobile continuum is only subject to gas transport between itself and the mobile continuum, and the mass transfer rate in Equation (7) based on the mass balance for the immobile continuum can be expressed according to Equation (11):

$$q_{im} = -\frac{\partial \rho_{m,i}}{\partial t} = -B^*Ce^{-Bt} \qquad (11)$$

The gas pressure(s) values can be used in accordance with the present invention for estimating rock sample 10 properties such as gas permeability using the pulse-decay test data in Equation (12):

$$\frac{\partial q}{\partial x} = -A\frac{\partial p}{\partial t} + q_{im}(t) \qquad (12)$$

wherein the mass transfer rate is assumed to be uniformly distributed along the longitudinal (lengthwise) direction of sample 10. The gas pressure (in the mobile continuum) along rock sample 10 is assumed to be a linear function of position according to Equation (13):

$$p = p_u + \frac{p_d - p_u}{L}x = p_u + \frac{\Delta p}{L}x \qquad (13)$$

where $p_u$ represents the gas pressure at upstream reservoir 20; $p_d$ represents the gas pressure at downstream reservoir 25; and L is the length of rock sample 10.

Equations (12) and (13) can be combined and integrated to express for gas mass flux (q) in rock sample 10 in accordance with Equation (14):

$$q = q_0 - A\left[\frac{dp_u}{dt}x + \frac{1}{2}\frac{x^2}{L}\frac{d(\Delta p)}{dt}\right] + q_{im}x \qquad (14)$$

where $q_0$ represents the gas mass flux at the inlet of rock sample 10 (x=0) (in connection with upstream reservoir 20). The gas mass flux at the outlet of the rock sample 10 (in connection with downstream reservoir 25), $q_L$, can be obtained from Equation (14) where x=L and expressed as Equation (15):

$$q_L = q_0 - AL\left[\frac{dp_u}{dt} + \frac{1}{2}\frac{d(\Delta p)}{dt}\right] + q_{im}L \qquad (15)$$

The gas mass fluxes $q_0$ and $q_L$ can be related to $p_u$ and $p_d$ as shown in Equation (16):

$$q_0 + q_L = \frac{2K}{L}(p_u - p_d) - \frac{AL}{6}\frac{d(p_d - p_u)}{dt} \tag{16}$$

by determining the mass balance within upstream reservoir 20 and downstream reservoir 25. The mass balance within upstream reservoir 20 can be expressed according to Equation (17):

$$\frac{d(v\rho_u)}{dt} = -A_r q_0 \tag{17}$$

wherein v represents the gas reservoir volume, $\rho_u$ is the gas density in upstream reservoir 20, and $A_r$ is the cross-sectional area of rock sample 10. In some embodiments, upstream reservoir 20 and downstream reservoir 25 have or can be assumed to have the same gas reservoir volume (v) for optimization of the pulse-decay test results as described in Jones, "A Technique for Fast Pulse-Decay Permeability Measurements in Tight Rocks," *SPEFE* 19-25 (March 1997).

The gas density is related to pressure through gas compressibility ($c_g$) in accordance with Equation (18):

$$c_g = \frac{1}{\rho}\frac{d\rho}{dp} \tag{18}$$

In certain embodiments, the gas compressibility can be approximated as a constant value in analyzing the pulse-decay test data at the late-time stage because of the small gas pressure variation as described, e.g. in Cui et al., "Measurements of Gas Permeability and Diffusivity of Tight Reservoir Rocks: Different Approaches and Their Applications," *Geofluids* 9, 208-223 (2009) such that the gas mass flux $q_0$ can be determined using Equation (19):

$$q_0 = -\frac{vc_g\rho_u}{A_r}\frac{dp_u}{dt} \tag{19}$$

In some embodiments, the gas mass flux $q_L$ can be determined using Equation (20):

$$q_L = \frac{vc_g\rho_d}{A_r}\frac{dp_d}{dt} \tag{20}$$

Within the context of the present invention, a positive gas mass flux $q_0$ results in a negative pressure change in upstream reservoir 20 and a corresponding positive pressure change in downstream reservoir 25.

The combination of equations (16), (19), and (20) can be expressed as follows:

$$\ln(p_u - p_d) = -st + E \tag{21}$$

where E is a constant and the slope s can be expressed as shown in Equation (22):

$$s = \frac{2K}{L\left(\frac{vc_g\rho}{A_r} + \frac{AL}{6}\right)} \tag{22}$$

The determination of the slope (s) in Equation (22) can be determined from the resulting pulse-decay test data and can be used to estimate the gas conductivity (K) such that the gas permeability can be determined or estimated based on the relationship $K = k\rho/\mu$ for rock sample 10 in accordance with the present invention. The relationship between gas permeability (or conductivity) and the pressure difference between upstream reservoir 20 and downstream reservoir 25 in accordance with Equations (21) and (22), respectively, is independent of any mass transfer occurrence between the mobile continuum and immobile continuum.

Equation (23) (below) can be used to determine the mass conservation within the pulse-decay system such that the loss rate of gas in upstream reservoir 20 and downstream reservoir 25 (expressed as $q_0 - q_L$) is equal to the increase rate of gas storage in the mobile continuum $$\left(AL\frac{d(p_u + p_d)}{dt}\right)$$

plus the rate of mass transfer from the mobile continuum to the immobile continuum ($q_{im}L$).

$$q_0 - q_L = AL\frac{d(p_u + p_d)}{dt} - q_{im}L \tag{23}$$

The mass transfer rate from the immobile continuum can, in certain embodiments, be expressed in accordance with Equation (24):

$$q_{im} = \left[\frac{A}{2} + \frac{vc_g\rho}{A_r L}\right]\frac{d(p_u + p_d)}{dt} \tag{24}$$

In accordance with some embodiments of the present invention, the pulse-decay system is initially in equilibrium and then disturbed by a (positive) pressure pulse from upstream reservoir 20. The resulting pressure subsequently increases in the mobile continuum. The pressure in the immobile continuum can increase relatively slowly with system gas flowing from the mobile continuum to the immobile continuum. Because pressure propagates quickly in the mobile continuum, it can be expected that the immobile continuum has a lower pressure than the mobile continuum at the late-time stage. For a given rock sample 10, $d(p_u + p_d)/dt$ is negative if rock sample 10 exhibits dual-continuum characteristics.

In accordance with the present invention, the $d(p_u + p_d)/dt$ data can be used to estimate the apparent mass transfer coefficient B for modeling gas transport in rock sample 10 using the dual-continuum approach as expressed in Equation (25):

$$\ln\left|\frac{d(p_u + p_d)}{dt}\right| = -Bt + F \tag{25}$$

where F is a constant.

In alternative embodiments, B values can be estimated directly from the pulse-decay test data and determined in accordance with Equation (26):

$$\ln\left(\frac{P_{av} - P_\infty}{P_\infty}\right) = G - Bt \qquad (26)$$

where $P_{av}=(p_u+p_d)/2$, G represents a constant, and $P_\infty$ is the resulting gas pressure when the mobile continuum and the immobile continuum reach equilibrium. In accordance with the present invention, $P_\infty$ can be determined by averaging between at least two (2) pressure measurements and ten (10) pressure measurements, alternately by averaging more than two pressure measurements, and alternately by averaging less than ten pressure measurements taken when the pressure stabilizes and equilibrium is established between the mobile continuum and immobile continuum.

Figure 3:
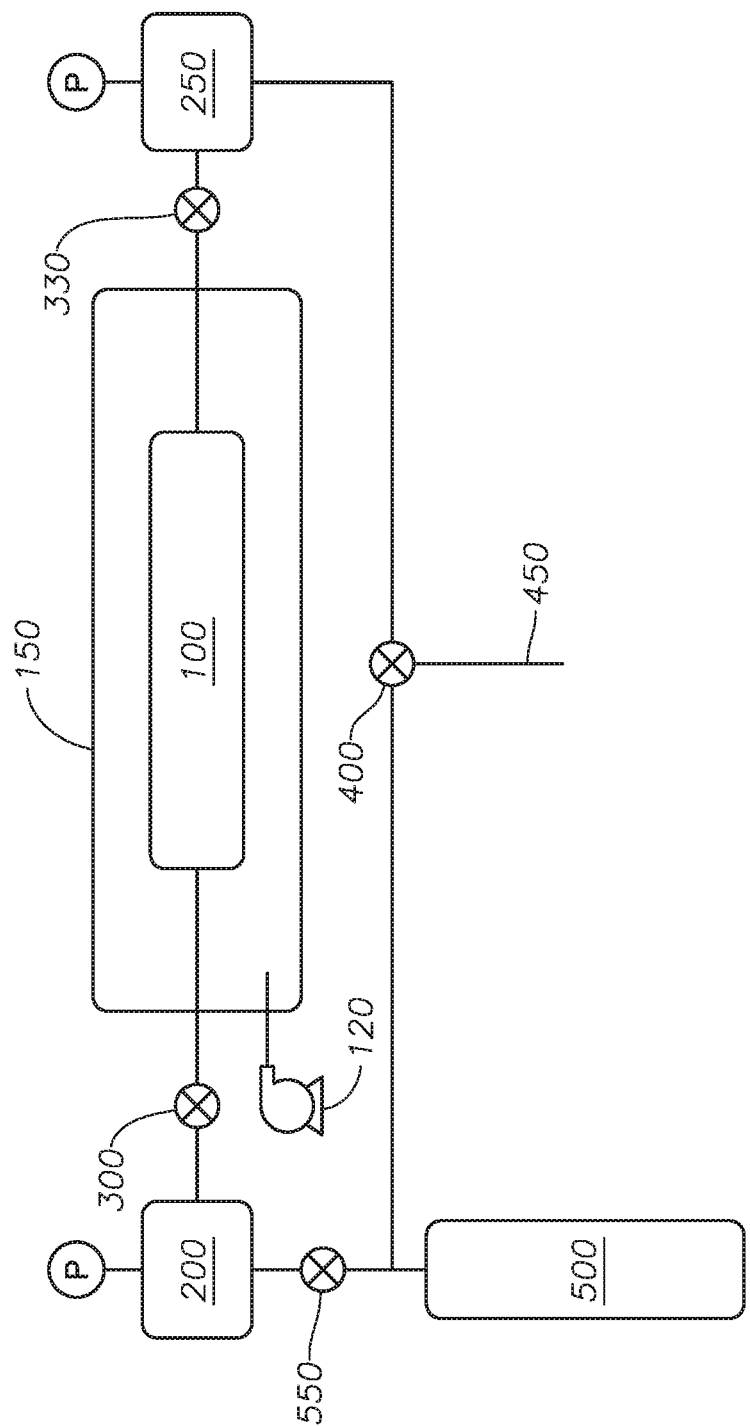
FIG. 3 shows a dual-continuum test system for gathering dual-continuum test data.

In a second method to estimate dual-continuum behavior, a dual-continuum test system is used. Referring to FIG. 3, a dual-continuum test system according to the present invention is provided. Reservoir sample 100 is placed in sample holder 150. Reservoir sample 100 can be isolated from any subterranean reservoir formation about which information is desired. The subterranean reservoir formations can include limestone, sandstone, and shale. In at least one embodiment, reservoir sample 100 can be a cylinder having a length and a diameter. In at least one embodiment, the length of reservoir sample 100 is in a range of between about 0.1 inches to about 16 inches. In at least one embodiment, the diameter is in the range of between about 0.1 inches to about 4 inches. In at least one embodiment, the length is smaller than the diameter. At the start of the dual-continuum test, the dual-continuum test system is in equilibrium with a uniform gas pressure. Uniform gas pressure can be achieved by filling upstream gas reservoir 200, downstream gas reservoir 250, and reservoir sample 100 with a gas to a gas pressure. Examples of gases that can be used to fill the dual-continuum test system include carbon dioxide, helium, and argon. The gas pressure can be between about 1000 psi and about 10,000 psi, alternately between about 2,000 psi and 8,000 psi, and alternately between about 4,000 psi and 6,000 psi. In at least one embodiment, the gas pressure is 5,000 psi. The dual-continuum test system is allowed to stabilize at which point the gas pressure is at a uniform gas pressure. After a uniform gas pressure is reached, upstream valve 300 is closed, closing off the connection between upstream gas reservoir 200 and reservoir sample 100. At the same time, downstream valve 350 is closed, closing off the connection between downstream gas reservoir 250 and reservoir sample 100. The pressure in upstream gas reservoir 200 and the pressure in downstream gas reservoir 250 are both adjusted to an adjusted pressure, where the adjusted pressure can be above or below the uniform gas pressure. The absolute difference between the uniform gas pressure and the adjusted pressure can be from between about 10 psi to 1000 psi. The pressure in upstream gas reservoir 200 and the pressure in downstream gas reservoir 250 are adjusted by the same amount. In at least one embodiment, the pressure in upstream gas reservoir 200 and downstream gas reservoir 250 are adjusted by adding additional gas from reservoir 500 through gas valve 550, such that the adjusted pressure is greater than the uniform gas pressure. In at least one embodiment, the pressure in upstream gas reservoir 200 and downstream gas reservoir 250 are adjusted by venting gas from the system using vent valve 400, which can be used to vent gas through vent 450, such that the adjusted pressure is less than the uniform gas pressure. The pressure in upstream gas reservoir 200 and the pressure in downstream gas reservoir 250 are allowed to stabilize at the adjusted pressure. To begin the dual-continuum test, upstream valve 300 and downstream valve 350 are opened simultaneously or nearly simultaneously. Opening upstream valve 300 and downstream valve 350 initiates the pressure-transient portion of the measurement by introducing pressure pulses from upstream gas reservoir 200 and downstream gas reservoir 250. Opening upstream valve 300 introduces a pressure pulse from upstream gas reservoir 200 due to the pressure in upstream gas reservoir 200 being different than the pressure in reservoir sample 100. Opening downstream valve 300 introduces a pressure pulse from downstream gas reservoir 250 due to the pressure in downstream gas reservoir 250 being different than the pressure in reservoir sample 100. The pressure in upstream gas reservoir 200, the pressure in downstream gas reservoir 250, or the pressure in both upstream gas reservoir 200 and downstream gas reservoir 250 are measured and recorded as a function of time (the "dual-continuum test data"). The pressure in sample holder 150 can be controlled by the confining pump 120. The dual-continuum test ends when the pressure in upstream gas reservoir 200 and in downstream gas reservoir 250 stabilizes. The dual-continuum test data is analyzed according to methods of the present invention to estimate a mass transfer coefficient.

Advantageously, the dual-continuum test system of the present invention, as shown in FIG. 3, removes the constraint that the gas flows from the upstream gas reservoir to the downstream gas reservoir through the reservoir sample. By doing so, the dual-continuum test can reduce the time to reach the late-time stage in the dual-continuum test system. When the late-time stage occurs earlier, the pressure differences observed can be attributed to the pressure differences in the two continua, which translates to the dual-continuum test data exhibiting stronger gas pressure signals corresponding to the flow behavior of a dual-continuum matrix. Advantageously, the dual-continuum test provides a method for increased accuracy of estimating the mass transfer coefficient in a shale matrix reservoir.

While in no way limiting the scope of the present invention, Equation (26) can also be derived using dual-continuum test data from a dual-continuum test system, as described with reference to FIG. 3. The pressure difference among upstream gas reservoir 200, downstream gas reservoir 250 and the mobile continuum are close at the late-time stage and the pressure within upstream gas reservoir 200 and downstream gas reservoir 250 can be approximately represented by $P_{av}=(P_u+P_d)/2$. Then, based on the mass balance principle, $$\frac{d(M_i + M^*)}{dt} = 0 \qquad (27)$$

where $M_i$ represents the total gas mass in the immobile continuum and $M^*$ represents the total gas mass in upstream gas reservoir 200, downstream gas reservoir 250, and the mobile continuum. In accordance with certain embodiments of the present invention, gas flow processes can be evaluated without involving gas adsorption, although in some embodiments gas adsorption can be considered as necessary. Gas masses can be related to gas densities in accordance with Equations (28) and (29):

$$M_i = V_{pi}\rho_i \qquad (28)$$

$$M^* = V\rho \qquad (29)$$

where $V_{pi}$ represents the total pore volume of the immobile continuum; V represents the summation of the total pore volume in the mobile continuum, the volume of upstream gas reservoir 200, and the volume of downstream gas reservoir 250; $\rho_i$ represents the gas density in the immobile continuum; and $\rho$ represents the gas density in upstream gas reservoir 200, downstream gas reservoir 250, and the mobile continuum. These densities can be related to gas pressures through Equation (18) with density in the coefficient term approximately being constant. Equation (18) and Equation (28) can be combined with Equation (29) to yield Equation (30):

$$\gamma \frac{dp_i}{dt} = -\frac{dP_{av}}{dt} \text{ where } \gamma = \frac{V_{pi}}{V}; \quad (30)$$

and $p_i$ is gas pressure in the immobile continuum. Equation (30) can be integrated and, assuming that $P_{av}=p_i=P_\infty$ for a time period (t) such as $t\rightarrow\infty$, gas pressures in accordance with certain embodiments of the present can be determined using Equation (31):

$$\gamma(p_i - P_\infty) = -(P_{av} - P_\infty) \quad (31)$$

Equation (31) can be rewritten as shown in Equation (32):

$$P_{av} - p_i = \left(1 + \frac{1}{\gamma}\right)(P_{av} - P_\infty) \quad (32)$$

Equations (8), (10), (30) and (32) can be combined such that the change in pressure within upstream gas reservoir 200 and downstream gas reservoir 250 over time can be determined according to Equation (33):

$$\frac{dP_{av}}{dt} = -B(1+\gamma)(P_{av} - P_\infty) \quad (33)$$

If $(1+\gamma)$ is approximated to be equal to one (1), the change in pressure within upstream gas reservoir 200 and downstream gas reservoir 250 can be written as follows:

$$\frac{dP_{av}}{dt} = -B(P_{av} - P_\infty) \quad (34)$$

Equation (34) can be integrated and, under conditions where $P_{av}=P_\infty$ for a time period (t) such as $t\rightarrow\infty$, can be expressed as Equation (26).

The methods and techniques of the present invention for estimating the mass transfer coefficient of a dual-continuum system are in the absence of a numerical inversion method. The methods and techniques of the present invention for a dual-continuum system advantageously eliminate the non-uniqueness parameter estimation that occurs with pulse-decay data (where the observations from the data can fit different combinations of parameters as compared to the pulse-decay data fitting one parameter).

The present invention provides a method of estimating the mass transfer coefficient between the two continua in a porous medium. It can be understood by one of skill in the art that estimating the mass transfer coefficient between two continua in a porous medium is not related to or relatable to estimating a mass transfer coefficient between a solid phase and liquid phase. The present invention is in the absence of single continuum model of a shale matrix.

In a second aspect of the present invention, a method for determining the properties of a petroleum reservoir in a subterranean formation is provided. The method includes the steps of isolating a subterranean shale reservoir sample capable of transferring or retaining a petroleum fluid; introducing the subterranean reservoir sample into an apparatus comprising two or more fluid reservoirs; equilibrating the pressure at a first pressure value within the apparatus; increasing the pressure in at least one of the fluid reservoirs using an inert gas; allowing sufficient time for the pressure in the two or more fluid reservoirs to equilibrate at a second pressure value; and measuring the properties of the reservoir sample. In certain aspects, the petroleum reservoir is composed of both macroporosities (mobile continuum) and microporosities (immobile continuum). In certain aspects, the macroporosity is composed of fracture porosity.

The method for estimating a mass transfer coefficient can be used to predict production rate in an active, prospective or reserve well. In at least one embodiment, the mass transfer coefficient can be used to more accurately predict a decline curve for gas production from a subterranean formation. In at least one embodiment, the decline curve can be used to calculate reserve oil or gas. In at least one embodiment of the present invention, the method for estimating mass transfer coefficient can be used to determine production data. The mass transfer from immobile continuum to mobile continuum can slow down decline of the gas production rate from a well with time. The mass transfer coefficient determined from the methods described herein can be used in a numerical simulator to calculate the decline curve of gas production rate.

EXAMPLES

The following examples are included to demonstrate preferred embodiments of the invention. It should be appreciated by those of skill in the art that the techniques and compositions disclosed in the examples which follow represent techniques and compositions discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or a similar result without departing from the spirit and scope of the invention.

Example 1

Example 1 tested the analytical solution developed to identify the dual-continuum behavior from pulse-decay test data sets for different rock samples. A data set for a granite sample and was provided by Stefan Finsterle at Lawrence Berkeley National Laboratory (Berkeley, Calif.). Data sets for both a limestone sample and black shale sample and were obtained from Xiangmin Zhang with PanTerra Geoconsultants (Leiderdorp, Netherlands). It was not expected that the granite sample or limestone sample would exhibit dual-continuum behavior, thus Example 1 was used to confirm the method of determining the mass transfer coefficient for a material that exhibits dual-continuum behavior.

Figure 4:
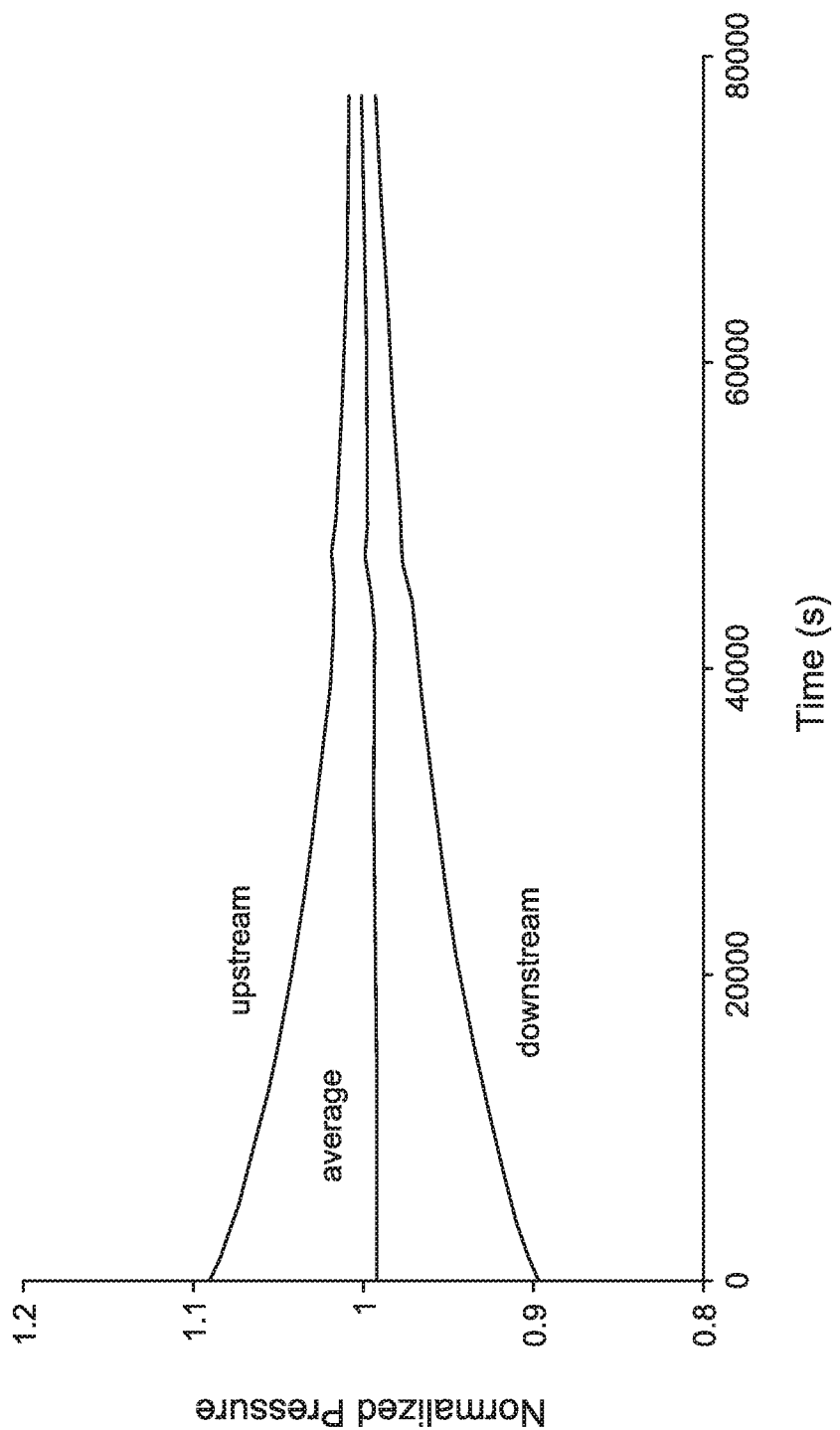
FIG. 4 shows a graphical representation of normalized shale gas pressure for an upstream reservoir, a downstream reservoir and an average of the upstream and downstream reservoirs as a function of time in accordance with embodiments of the present invention.

For both data sets, the first step was to normalize the pressure measurements by dividing the pressure measurements by the averaged pressure $(p_u+p_d)/2$, at the last data point. This normalization step allows the calculations to proceed using dimensionless pressures, but does not impact the estimation of parameter B, as shown in Eq. 33. FIG. 4 shows measurements for the black shale sample in terms of normalized pressure. Due to test issues related to confining stress control at about 50,000 s, pressure change is not smooth near that time. However, the late-time stage behavior is not impacted after that time. To estimate pressure change rate with time, the following approximation is used:

$$\frac{d(p_u^* + p_d^*)}{dt} \approx \frac{[p_u^*(t + \Delta t) + p_d^*(t + \Delta t)] - [p_u^*(t) + p_d^*(t)]}{\Delta t} \quad (35)$$

Where subscript * refers to the normalized pressure, and $\Delta t$ is the time interval for two adjacent measurements, that is 1 s for the granite, 10 s for the limestone, and 30 s for the black shale.

Figure 5:
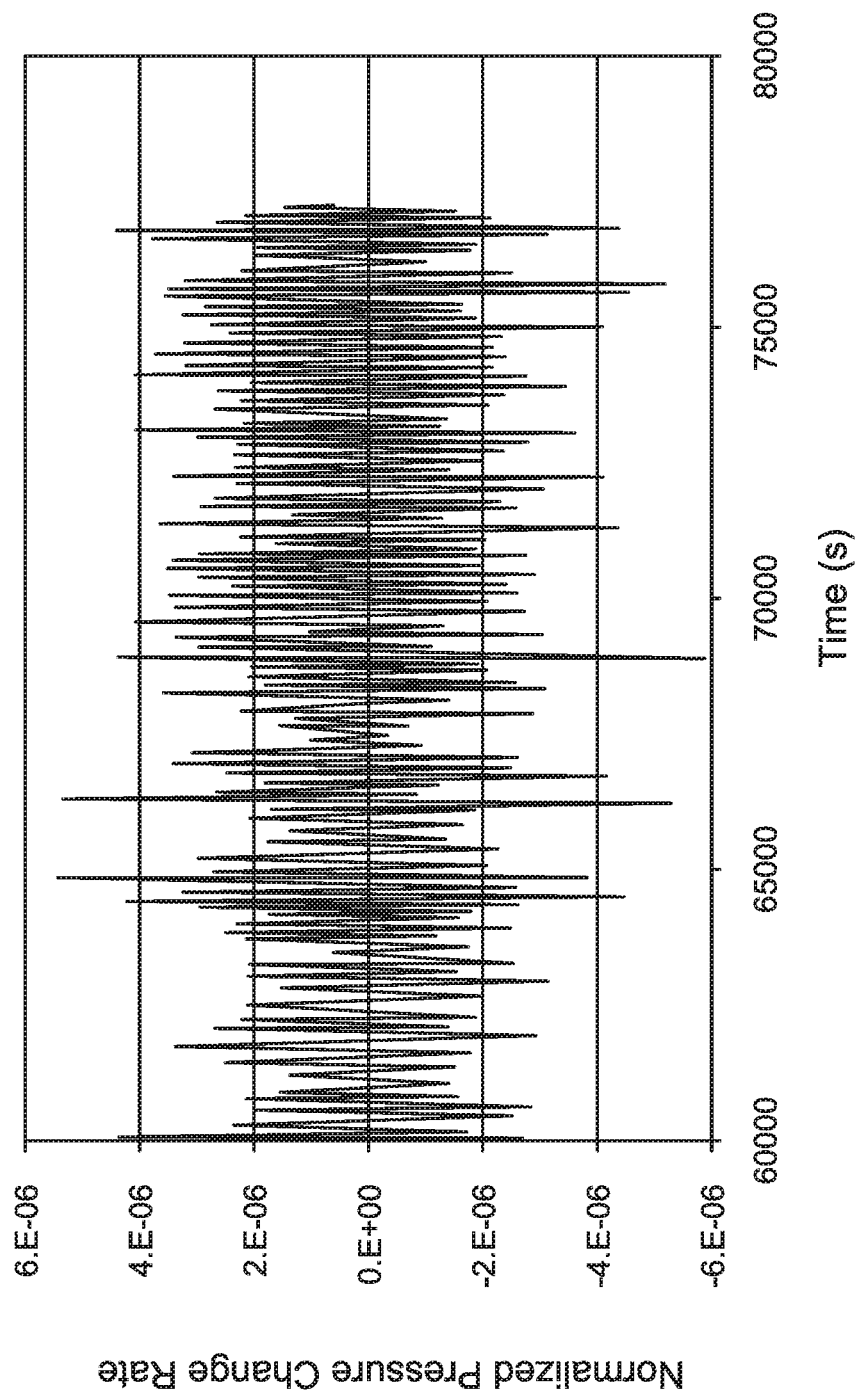
FIG. 5 shows a graphical representation of normalized shale gas pressure change rate for a subterranean reservoir sample as a function of time in accordance with embodiments of the present invention.

FIG. 5 provides a graphical view of the normalized pressure change rate data produced from equation 35. Dual-continuum flow behavior was not detected from the data sets for the granite sample and limestone sample. The single continuum behavior is indicated by the following two aspects. First, values of pressure change rate calculated from Eq. 35 fluctuate randomly around zero. In contrast, for a dual-continuum system, the pressure change rate should be constantly negative at the late-time stage of the pulse-decay test. Second, the pressure change rate values are on the order of $\pm 1.0E-5$ ($s^{-1}$) for both the granite sample and the limestone sample, and therefore are practically zero. Interestingly, observed pressure change rate data for the black shale sample has the same features, with the pressure change rate values being within the range of $\pm 6.0E-6$ ($s^{-1}$) and having an average value of 9.0E-8 ($s^{-1}$), as shown in FIG. 5. In this Example, the black shale sample does not show dual-continuum behavior or the dual-continuum behavior is too weak to be noticeable.

Example 2

Figure 6:
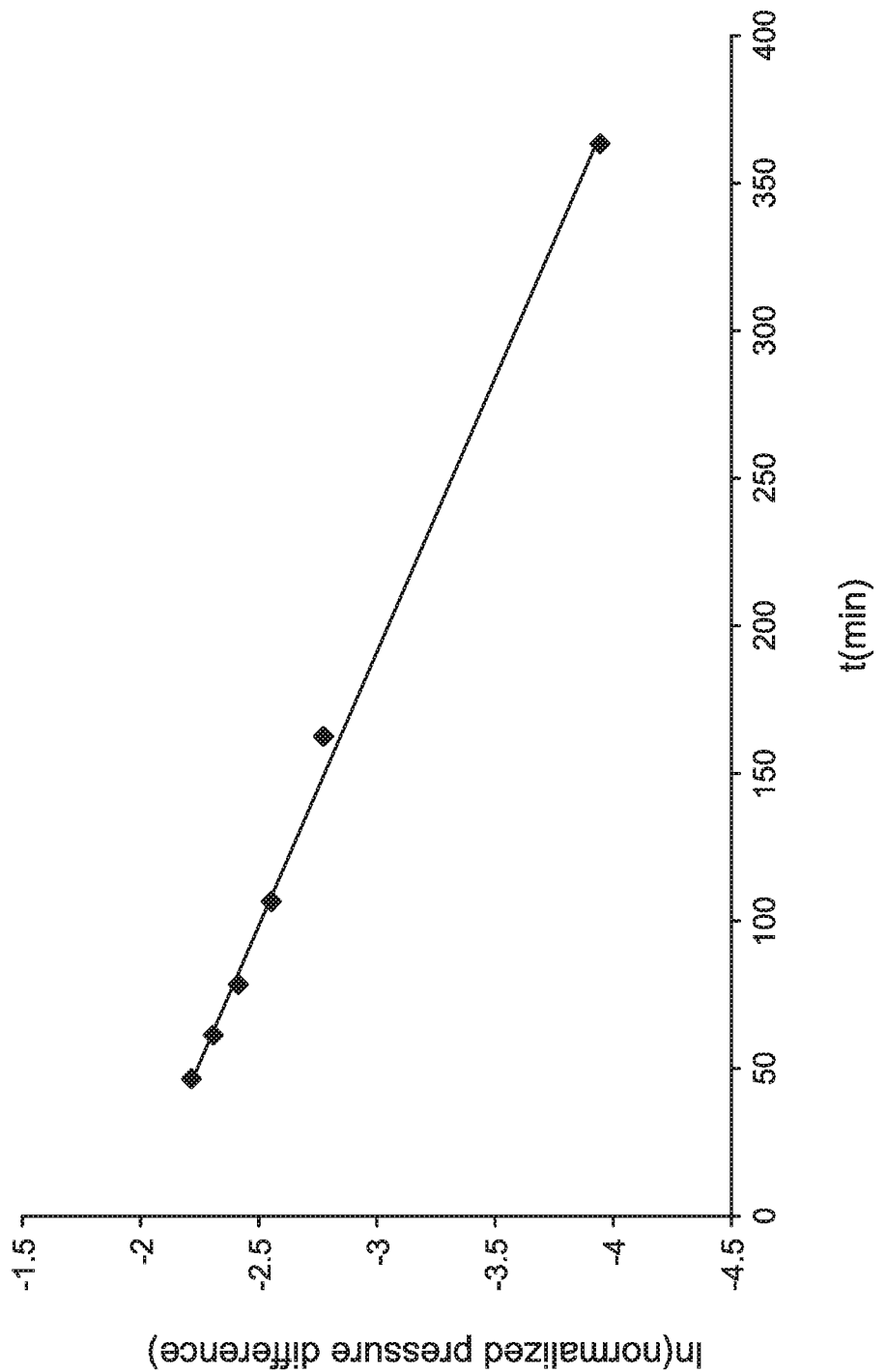
FIG. 6 shows a gas pressure plot for a subterranean reservoir sample at a confining pressure of about 1000 pounds per square inch (psi) as a function of time in accordance with embodiments of the present invention.

Example 2 tested the analytical solution developed to identify the dual-continuum behavior from pulse-decay test data sets from literature for different rock samples. Alnoaimi et al., ("Characterization and Measurement of Multi-Scale Gas Transport in Shale Core Samples," Paper URTeC 1920820, The Unconventional Resources Technology Conference, Denver, Colo., USA, Aug. 25-27, 2014) generated pulse-decay test data for a Haynesville shale (Louisiana or Texas) sample and an Eagle Ford shale (Texas) sample. Alnoaimi pulse-decay test used helium such that the adsorption is minimal. The Alnoaimi data demonstrated that after the upstream reservoir and downstream reservoir reach equilibrium ($p_u = p_d = P_{av}$), the gas pressure continues to decline with time. This is an obvious signature of dual-continuum gas flow behavior. In Example 2, the analytical solution was applied to analyze the gas pressure signal for the Eagle Ford shale sample under a confining stress of 1000 psi, because that sample exhibited the most dramatic pressure changes with time after the upstream reservoir and downstream reservoir reach equilibrium; the Haynesville samples correspond to much weaker pressure declines. FIG. 6 shows fitting of Eq. 34 to a number of data points (after 46 minutes) with a fitted mass transfer coefficient, B, of 0.0054 $min^{-1}$. It should be noted that the analytical method of the present invention assumes the upstream reservoir and the downstream reservoir contain the same volume, whereas the Alnoaimi pulse-decay test used two different volumes for the gas reservoirs. However, as can be seen from the derivation, this condition is not needed when $p_u = p_d$. In other words, it is valid to apply Eq. 34 to analyze the Alnoaimi data when $p_u = p_d$. The analytical method of the present invention confirms that the Alnoaimi data exhibits dual-continuum behavior.

Example 3

Figure 7:
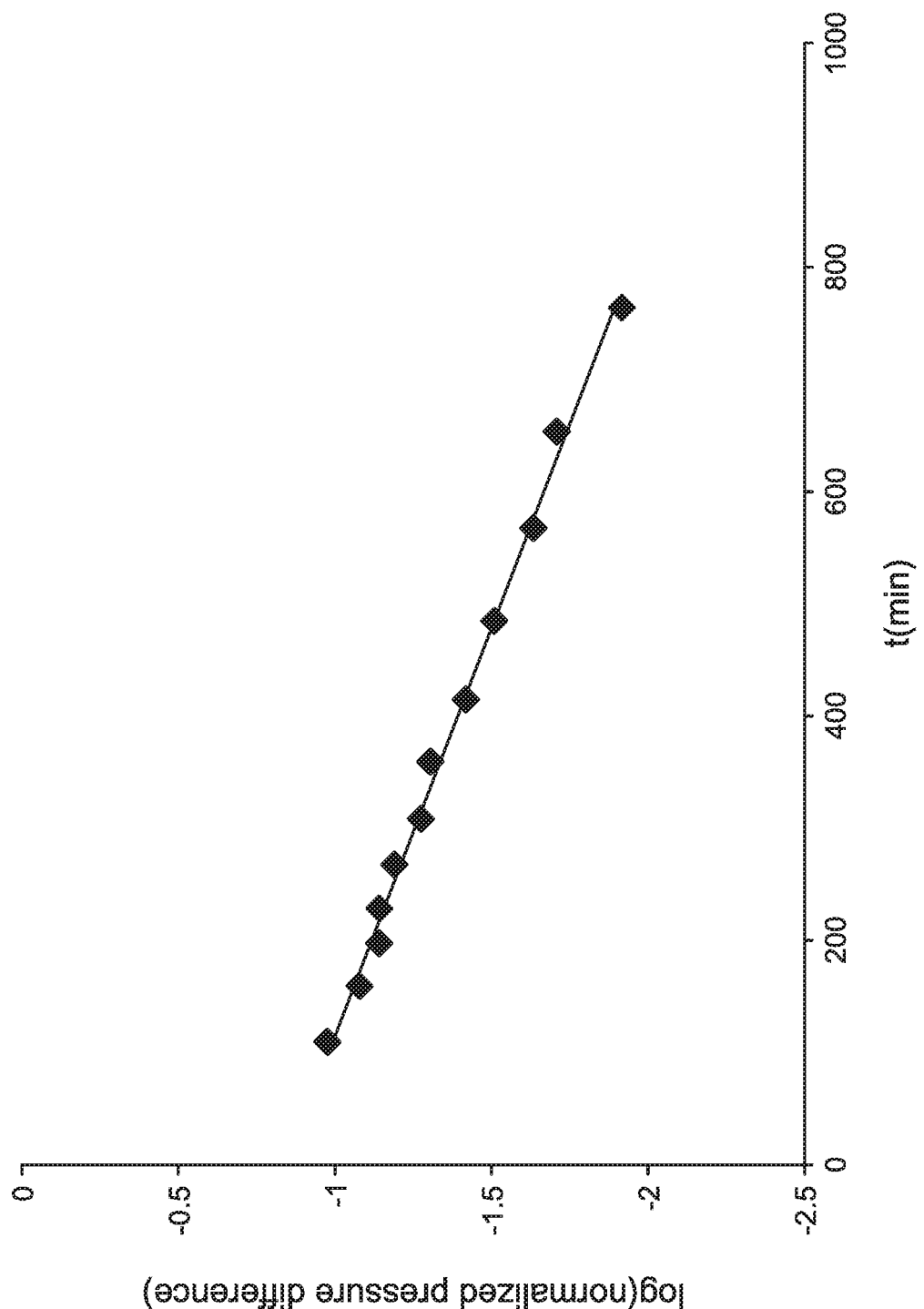
FIG. 7 shows a gas pressure plot as a function of time that shows the fitted mass transfer coefficient.

Example 3 tested the analytical solution developed to identify the dual-continuum behavior from pulse-decay test data sets from literature for a Barnett Shale sample (Texas). Bhandari et al., ("Anisotropy and stress dependence of permeability in the Barnett Shale." Transp Porous Med 2015, DOI 10.1007/s11242-015-0482-0) generated pulse-decay test data for the Barnett Shale that showed no visible fractures in the samples. Argon gas was used as the pore fluid. The analytical method was used to analyze the data under a confining stress of 4003 psi. FIG. 7 shows fitting of Eq. 34 to a number of data points (after 109 minutes) with a fitted mass transfer coefficient, B, of 0.0014 $min^{-1}$. While comparable to the mass transfer coefficient value for the Eagle Ford shale sample in Example 2, the mass transfer coefficient value for Example 3 is a factor of 4 smaller, meaning that the Barnett shale sample of Example 3 exhibits a stronger dual-continuum behavior than the Eagle Ford shale sample of Example 2.

The dual-continuum test data are fitted by appropriate analytical solutions in which permeability can be estimated using Equation (21) and the mass transfer coefficient can be determined using Equation (26). Both permeability and mass transfer coefficient can be estimated using a pulse-decay test system, such as the one shown in FIG. 2. Mass transfer coefficient can be estimated using a dual-continuum test system, such as the one shown in FIG. 3. At the late-time stage, the pressure difference across the dual-continuum test system is generally small and parameters are assumed to be constant. In this case, the permeability can be determined based on the slope from the plot of log of the pressure difference as a function of time using Equation (21), while the mass transfer coefficient can be determined based on the slope from the plot of a function (e.g. a logarithmic function) of the average pressure as a function of time using Equation (26).

Although the present invention has been described in detail, it should be understood that various changes, substitutions, and alterations can be made hereupon without departing from the principle and scope of the invention. Accordingly, the scope of the present invention should be determined by the following claims and their appropriate legal equivalents.

The singular forms "a", "an" and "the" include plural references, unless the context clearly dictates otherwise.

"Optional" or "optionally" means that the subsequently described component may or may not be present or the event or circumstances may or may not occur. The description includes instances where the component is present and instances where it is not present, and instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

Throughout this application, where patents or publications are referenced, the disclosures of these references in their entireties are intended to be incorporated by reference into this application, in order to more fully describe the state of the art to which the invention pertains, except when these references contradict the statements made herein.

NOMENCLATURE (For the following factors, constants and operators, L=length, M=mass, T=time)
A=a parameter defined in Equation (4), $L^{-2} T^2$
$A_r$=area of cross section of core sample defined in Equation (17), $L^2$
B=apparent mass transfer coefficient defined in Equation (10), $T^{-1}$
B*=mass transfer coefficient defined in Equation (8), $L^{-2}T$
C=a constant in Equation (9)
$c_g$=gas compressibility defined in Equation (18), $T^2L^{-1}M^{-1}$
F=a constant in Equation (25)
G=a constant in Equation (26)
K=gas flow conductivity defined in Equation (5), T
k=permeability, $L^2$
L=length of core sample, L
$M_i$=total gas mass in the immobile continuum, M
M*=total gas mass in the mobile continuum and gas reservoirs, M
p=gas pressure, $FL^{-2}$
$p_i$=gas pressure in immobile continuum, $ML^{-1}T^{-2}$
$p_u$=gas pressure in upstream gas reservoir, $ML^{-1}T^{-2}$
$p_d$=gas pressure in downstream gas reservoir, $ML^{-1}T^{-2}$
$p_\infty$=average gas pressure for the two gas reservoirs, $ML^{-1}T^{-2}$
$p_\infty$=gas pressure at t→∞, $ML^{-1}T^{-2}$
p*=a pseudo pressure defined in Equation (6), $ML^{-3}T^{-1}$
q=gas mass flux, $ML^{-2}T^{-1}$
$q_0$=gas mass flux from upstream gas reservoir to core sample, $ML^{-2}T^{-1}$
$q_L$=gas mass flux from core sample to the downstream gas reservoir, $ML^{-2}T^{-1}$
$q_{im}$=mass transfer rate (per unit volume of the porous medium) from the immobile continuum, $ML^{-3}T^{-1}$
s=slope given in Equation (22), $T^{-1}$
t=time, T
V=summation of pore volume in the mobile continuum and volumes of the two gas reservoirs, $L^3$
$V_{pi}$=total pore volume in immobile continuum, $L^3$
v=volume of gas reservoirs, $L^3$
x=location, L
μ=gas viscosity, $MT^{-1}L^{-1}$
ρ=gas density in the mobile continuum, $ML^{-3}$
$\rho_i$=gas density in the immobile continuum, $ML^{-3}$
$\rho_d$=gas density in the downstream gas reservoir, $ML^{-3}$
$\rho_u$=gas density in the upstream gas reservoir, $ML^{-3}$
$\mu_m$=apparent gas density in the mobile continuum defined in Equation (2), $ML^{-3}$
$\rho_a$=absorbed gas density in the mobile continuum, $ML^{-3}$
ϕ=porosity of the mobile continuum
γ=dimensionless volume ratio defined in Equation (30)

What is claimed is:

1. A method of determining a flow characteristic of a subterranean reservoir formation for the purpose of predicting production capabilities, the method comprising the steps of:
obtaining a reservoir sample from the subterranean reservoir formation;
creating a plurality of pressure pulses across the reservoir sample;
obtaining from the reservoir sample dual-continuum test data, where the dual-continuum test data comprises late-time stage pressure data;
determining a mass transfer coefficient from the dual-continuum test data, wherein the mass transfer coefficient indicates a mass flow rate between two continua of the subterranean reservoir formation divided by a gas pressure difference between the two continua per unit bulk volume of the subterranean reservoir formation; and
determining the flow characteristic from the mass transfer coefficient.

2. The method of claim 1, where the subterranean formation is selected from the group consisting of limestone, sandstone, and shale.

3. The method of claim 1, where the dual-continuum test data is obtained from a dual-continuum test system.

4. The method of claim 1, where the step of obtaining from the reservoir sample the dual-continuum test data further comprises the steps of:
placing the reservoir sample in a sample holder, where the reservoir sample is fluidly connected to an upstream gas reservoir and a downstream gas reservoir, where the sample holder is configured to apply a hydrostatic confining stress to reservoir sample;
filling the upstream gas reservoir, the downstream gas reservoir, and the reservoir sample with a gas to a gas pressure;
closing an upstream valve, where closing the upstream valve isolates upstream gas reservoir from both the downstream gas reservoir and the reservoir sample;
closing a downstream valve, where closing the downstream valve isolates downstream gas reservoir from both the upstream gas reservoir and the sample holder;
increasing the pressure in the upstream gas reservoir to a test pressure;
increasing the pressure in the downstream gas reservoir to the test pressure;
opening the upstream valve generally at the same time the downstream valve is opened such that a plurality pressure pulse is created from the upstream gas reservoir and the downstream gas reservoir; and
measuring the pressure data in the upstream gas reservoir and the downstream gas reservoir.

5. The method of claim 1, wherein the flow characteristic is dual-continuum flow.

6. The method of claim 1, wherein the flow characteristic is a function of an immobile continuum and a mobile continuum in the reservoir sample.

7. The method of claim 4, where the gas pressure in the upstream gas reservoir, the downstream gas reservoir, and the reservoir sample is between 1000 psi and 10,000 psi.

8. The method of claim 4, where the gas is selected from the group consisting of carbon dioxide, helium, nitrogen, and argon.

9. A system to measure dual-continuum test data, the system comprising:
a sample holder, the sample holder configured to secure a reservoir sample;
an upstream gas reservoir fluidly connected to the sample and a downstream gas reservoir;
a downstream gas reservoir fluidly connected to the sample and the upstream gas reservoir;

an upstream valve, the upstream valve configured to isolate the upstream gas reservoir from both the sample and the downstream gas reservoir; and a downstream valve, the downstream valve configured to isolate the downstream gas reservoir from both the sample and the upstream gas reservoir, wherein a mass transfer coefficient is determined from the dual-continuum test data, the mass transfer coefficient indicating a mass flow rate between two continua of the reservoir formation divided by a gas pressure difference between the two continua per unit bulk volume of the reservoir formation.

10. A method of determining a flow characteristic of a subterranean reservoir formation for the purpose of predicting production capabilities, the method comprising the steps of:

obtaining dual-continuum test data, where the dual-continuum test data represents the subterranean reservoir formation;

determining a mass transfer coefficient from the dual-continuum test data, wherein the mass transfer coefficient indicates a mass flow rate between two continua of the subterranean reservoir formation divided by a gas pressure difference between the two continua per unit bulk volume of the subterranean reservoir formation; and determining the flow characteristic from the mass transfer coefficient.

11. The method of claim 10, where the subterranean formation is selected from the group consisting of limestone, sandstone, and shale.

12. The method of claim 10, where the dual-continuum test data is obtained from a dual-continuum test system.

13. The method of claim 10, wherein the flow characteristic is dual-continuum flow.

14. The method of claim 10, wherein the flow characteristic is a function of an immobile continuum and a mobile continuum in the reservoir sample.

* * * * *